United States Patent
Zhang et al.

(10) Patent No.: US 9,676,736 B2
(45) Date of Patent: Jun. 13, 2017

(54) 4-SUBSTITUENT-2-HYDROXYLMORHOLINE-3-ONE AND PREPARATION METHOD THEREOF

(71) Applicants: Zhejiang Hisun Pharmaceutical Co., Ltd., Zhejiang (CN); Shanghai Institute of Pharmaceutical Industry, Shanghai (CN)

(72) Inventors: Fuli Zhang, Shanghai (CN); Chonghao Liu, Shanghai (CN); Pengcheng Qiu, Shanghai (CN); Jian Chai, Zhejiang (CN); Qingfeng Cai, Zhejiang (CN)

(73) Assignee: Zhejiang Hisun Pharmaceutical Co., Ltd., Zhejiang (CN)

( * ) Notice: Subject to any disclaimer, the term of this patent is extended or adjusted under 35 U.S.C. 154(b) by 0 days.

(21) Appl. No.: 14/394,041

(22) PCT Filed: Apr. 15, 2013

(86) PCT No.: PCT/CN2013/074202
§ 371 (c)(1),
(2) Date: Oct. 10, 2014

(87) PCT Pub. No.: WO2013/152741
PCT Pub. Date: Oct. 17, 2013

(65) Prior Publication Data
US 2015/0087828 A1    Mar. 26, 2015

(30) Foreign Application Priority Data

Apr. 13, 2012   (CN) .......................... 2012 1 0112140

(51) Int. Cl.
*C07D 265/32*     (2006.01)
*C07D 413/06*     (2006.01)
(52) U.S. Cl.
CPC ......... *C07D 265/32* (2013.01); *C07D 413/06* (2013.01)
(58) Field of Classification Search
CPC ............................ C07D 265/32; C07D 413/06
See application file for complete search history.

(56) References Cited

U.S. PATENT DOCUMENTS

| 7,618,960 B2 * | 11/2009 | Kimura | ............... C07D 401/10 514/230.5 |
| 2002/0042510 A1 | 4/2002 | Crocker et al. | |
| 2002/0052493 A1 | 5/2002 | Brands et al. | |

FOREIGN PATENT DOCUMENTS

| CN | 1436178 A | 8/2003 |
| CN | 101312965 A | 11/2008 |
| CN | 102153522 A | 8/2011 |
| CN | 102675240 A | 4/2012 |
| JP | 2011514892 A | 5/2012 |
| WO | WO 01/94322 A1 | 12/2001 |
| WO | WO 01/96319 A1 | 12/2001 |
| WO | WO 2007/060810 A1 | 5/2007 |
| WO | WO 2009/106486 A1 | 9/2009 |

OTHER PUBLICATIONS

Chinese Office Action, dated Sep. 11, 2013, from corresponding Chinese Application No. 201210112140.9.
Japanese Office Action, dated Aug. 25, 2015, from corresponding Japanese Patent Application No. 2015-504859.
Y Chen et al.:*Study of lactol activation by trifluroacetic anhydride via in situ Fourier transform infared spectroscopy*, vol. 497, 2003, Anayltica Chimica Acta pp. 154-164.
Greene T.W. and Wuts P.G.M., Protective Groups in Organic Chemistries, 1991, p. 390.
International Search Report dated Jul. 25, 2013 from corresponding International Application No. PCT/CN2013/074202.
Nelson, T.D., S ntheses of morpholine-2,3-diones and 2-hydroxymorpholin-3-ones: intermediates in the synthesis of aprepitant, Tetrahedron Letters 45 (2004) 8917-8920, 2004 Elsevier Ltd, Merck Research Laboratories, pp. 8917-8920.
Brands, K.M., et al., Efficient Synthesis of NK$_1$ receptor Antagonist Aprepitant Using a Crystallization-Induced Diastereoselective Transformation, J. Am. Chem. Soc. 2003, 125, pp. 2129-2135, published Jan. 30, 2003.
J. Am. Chem. Soc. 2003, 125, 2129-2135, Supporting Information pp. S1-S33.

\* cited by examiner

*Primary Examiner* — Rebecca Anderson
(74) *Attorney, Agent, or Firm* — Wolf, Greenfield & Sacks, P.C.

(57) ABSTRACT

A molecule with neural activities, especially 4-substituent-2-hydroxymorpholin-3-one, as a new intermediate of neurokinin-1 receptor antagonist aprepitant, and preparation method thereof.

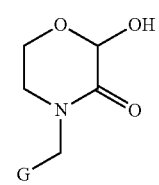

20 Claims, No Drawings

4-SUBSTITUENT-2-HYDROXYLMORPHOLINE-3-ONE AND PREPARATION METHOD THEREOF

FIELD OF THE INVENTION

The present invention relates to the field of pharmaceutical chemistry, and particularly to an intermediate of aprepitant of Formula I, compound 4-substituent-2-hydroxymorpholin-3-one, and the preparation method thereof.

BACKGROUND OF THE INVENTION

Aprepitant, the chemical name of 5-[[(2R,3S)-2-[(R)-1-[3,5-bis(trifluoromethylphenyl)ethoxy]-3-(4-fluorophenyl)-4-morpholin yl]methyl]-1,2-dihydro-3H-1,2,4-triazol-3-one, has the structure of Formula V:

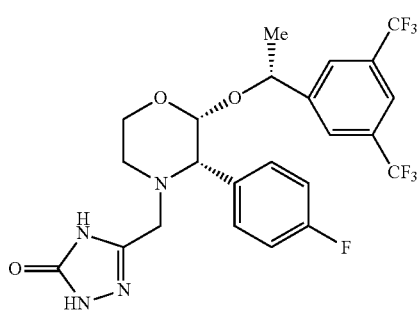

V

Aprepitant is the first neurokinin-1 (NK-1) receptor antagonist developed by Merck Company, USA. This medicine can pass through the blood brain barrier, and antagonize NK-1 receptor with high selectivity, so as to block the effect of substance P, and additionally, it has lower affinity to NK-2 and NK-3. Aprepitant is clinically used for the prevention of nausea and vomiting due to chemotherapy, as well as postoperative nausea and vomiting. Aprepitant was marketed in 2003 under the trade name of Emend.

In the synthetic route reported by Karel M. J. Brands et al. in J. AM. CHEM. SOC. 2003, 125, 2129-2135, the compound of Formula VII is an important intermediate, which can be synthesized by the condensation reaction of aqueous glyoxalic acid solution and the compound of Formula VI as the starting material, which has the following reaction equation:

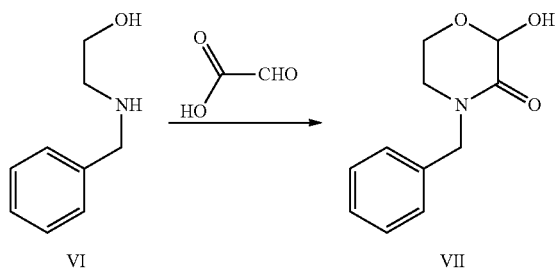

VI                                    VII

Additionally, another preparation method for the compound of Formula VII was also reported by Todd D. Nelson in Tetrahedron Letters 45 (2004) 8917-8920. In this method, the compound of Formula VII was obtained by reducing the compound of Formula VIII using lithium tri-sec-butyloborohydride, in which the compound of Formula VIII was obtained by the reaction of the compound of Formula VI and diethyl oxalate. However, the yield of this method is low, and the reducing agent lithium tri-sec-butylborohydride is demanded, which is inflammable, corrosive and expensive, so that this is not favorable for industrial production.

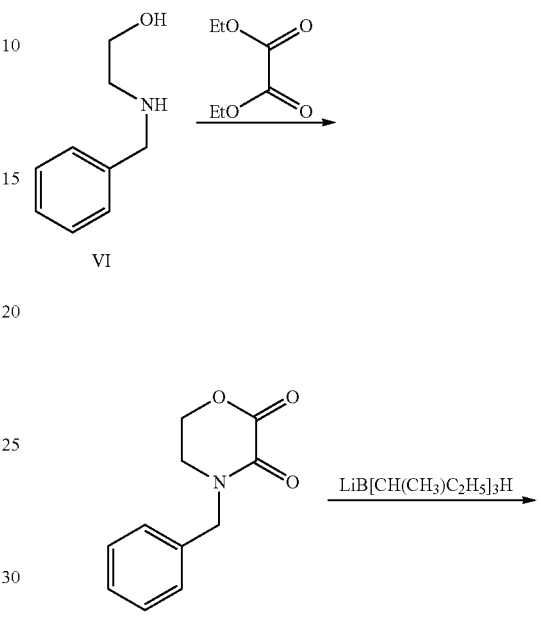

VI

VIII

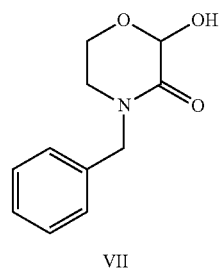

VII

In the present invention, 4-substituent-2-hydroxymorpholin-3-one is obtained by the condensation reaction of aqueous glyoxalic acid solution and the compound of Formula IV as the starting material. Especially, when electron-withdrawing substituents are bonded to the benzene ring, the yield of 4-substituent-2-hydroxymorpholin-3-one can be enhanced significantly.

SUMMARY OF THE INVENTION

The present invention provides a molecule with neural activities, especially 4-substituent-2-hydroxymorpholin-3-one(I), as a new intermediate of neurokinin-1 receptor antagonist aprepitant, and preparation method thereof. When electron-withdrawing substituents are bonded to the aryl, the yield of 4-substituent-2-hydroxymorpholin-3-one can be enhanced significantly and the reaction time becomes shorter, as compared to the method reported in J. AM. CHEM. SOC. 2003, 125, 2129-2135.

A class of novel compound, 4-substituent-2-hydroxymorpholin-3-one, has the structure of Formula I:

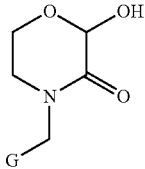

wherein, G is selected from:
(i) groups of Formula II

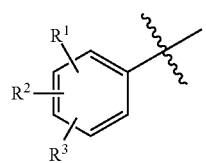

wherein,
$R^1$, $R^2$, and $R^3$ are independently selected from: hydrogen, substituted or unsubstituted $C_1$-$C_6$ alkyl, substituted or unsubstituted $C_2$-$C_6$ alkenyl, $C_2$-$C_6$ alkynyl, substituted or unsubstituted phenyl, halo-, —CN, —$CX_3$ (X is selected from Cl, Br, and F), —$NO_2$, —$SR^6$, —$SOR^6$, —$SO_2R^6$, —$(CH_2)_m$—$NR^4R^5$, —$NR^4COR^5$, —$NR^4CO_2R^5$, —$CONR^4R^5$, —$COR^4$, —$CO_2R^4$, hydroxyl, and $C_1$-$C_6$ alkoxy; the substituents on the $C_1$-$C_6$ alkyl and $C_2$-$C_6$ alkenyl can be independently selected from: hydroxyl, oxo-, $C_1$-$C_6$ alkoxy, phenyl, —CN, —$NO_2$, halo-, —$NR^4R^5$, —$NR^4COR^5$, —$NR^4CO_2R^5$, —$CONR^4R^5$, —$COR^4$, and —$CO_2R^4$; the substituents on the phenyl can be selected from: hydroxyl, $C_1$-$C_6$ alkyl, $C_1$-$C_6$ alkoxy, $C_2$-$C_6$ alkenyl, halo-, —CN, —$NO_2$, —$CF_3$, —$(CH_2)_m$—$NR^4R^5$, —$NR^4COR^5$, —$NR^4CO_2R^5$, —$CONR^4R^5$, —$COR^4$, and —$CO_2R^4$; and $R^1$, $R^2$, and $R^3$ can not be hydrogen at the same time;

preferably, $R^1$, $R^2$, and $R^3$ are independently selected from: hydrogen, unsubstituted $C_1$-$C_6$ alkyl, $C_1$-$C_6$ alkoxy, halogen, —$NO_2$, —CN, and —$CX_3$ (X is selected from Cl, Br, and F); and $R^1$, $R^2$, and $R^3$ can not be hydrogen at the same time;

further preferably, $R^1$, $R^2$, and $R^3$ are independently selected from: hydrogen, —$NO_2$, —Cl, and —$CF_3$; and $R^1$, $R^2$, and $R^3$ can not be hydrogen at the same time;

$R^4$ and $R^5$ are independently selected from: hydrogen, $C_1$-$C_6$ alkyl, monohydroxyl substituted $C_1$-$C_6$ alkyl, and phenyl;
$R^6$ is hydrogen or $C_1$-$C_6$ alkyl;
m is selected from 1, 2, 3 or 4;
(ii) groups of Formula III

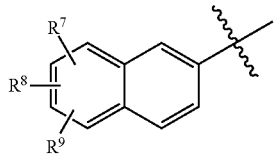

wherein,
$R^7$, $R^8$, and $R^9$ are independently selected from: hydrogen, substituted or unsubstituted $C_1$-$C_6$ alkyl, substituted or unsubstituted $C_2$-$C_6$ alkenyl, $C_2$-$C_6$ alkynyl, substituted or unsubstituted phenyl, halo-, —CN, —$CX_3$ (X is selected from Cl, Br, and F), —$NO_2$, —$SR^{12}$, —$SOR^{12}$, —$SO_2R^{12}$, —$(CH_2)_m$—$NR^{10}R^{11}$, —$NR^{10}COR^{11}$, —$NR^{10}CO_2R^{11}$, —$CONR^{10}R^{11}$, —$COR^{10}$, —$CO_2R^{10}$, hydroxyl, and $C_1$-$C_6$ alkoxy; the substituents on the $C_1$-$C_6$ alkyl and $C_2$-$C_6$ alkenyl are each independently selected from: hydroxyl, oxo-, $C_{1-6}$ alkoxy, phenyl, —CN, —$NO_2$, halo-, —$NR^{10}R^{11}$, —$NR^{10}COR^{11}$, —$NR^{10}CO_2R^{11}$, —$CONR^{10}R^{11}$, —$COR^{10}$, and —$CO_2R^{10}$; the substituents on the phenyl can be selected from: hydroxyl, $C_1$-$C_6$ alkyl, $C_1$-$C_6$ alkoxy, $C_2$-$C_6$ alkenyl, halo-, —CN, —$NO_2$, —$CF_3$, —$(CH_2)_m$—$NR^{10}R^{11}$, —$NR^{10}COR^{11}$, —$NR^{10}CO_2R^{11}$, —$CONR^{10}R^{11}$, —$COR^{10}$, and —$CO_2R^{10}$;

preferably, $R^7$, $R^8$, and $R^9$ are independently selected from: hydrogen, unsubstituted $C_1$-$C_6$ alkyl, $C_1$-$C_6$ alkoxy, halogen, —$NO_2$, —CN, and —$CX_3$ (X is selected from Cl, Br, and F); further preferably, $R^7$, $R^8$, and $R^9$ are hydrogen.

$R^{10}$ and $R^{11}$ are independently selected from: hydrogen, $C_1$-$C_6$ alkyl, monohydroxyl substituted $C_1$-$C_6$ alkyl, and phenyl;

$R^{12}$ is hydrogen or $C_1$-$C_6$ alkyl;

m is selected from 1, 2, 3, or 4.

Particularly, the compound of Formula I above are preferably selected from the following compounds:

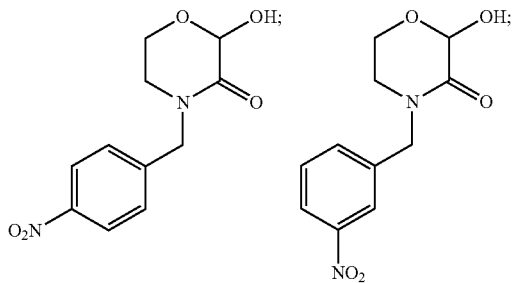

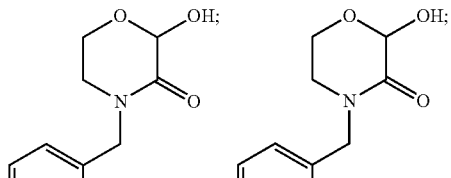

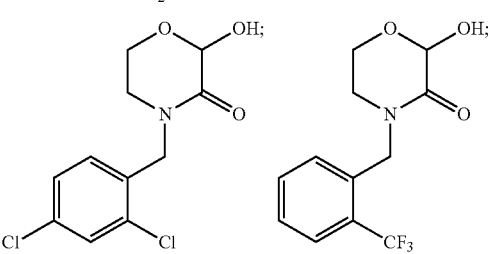

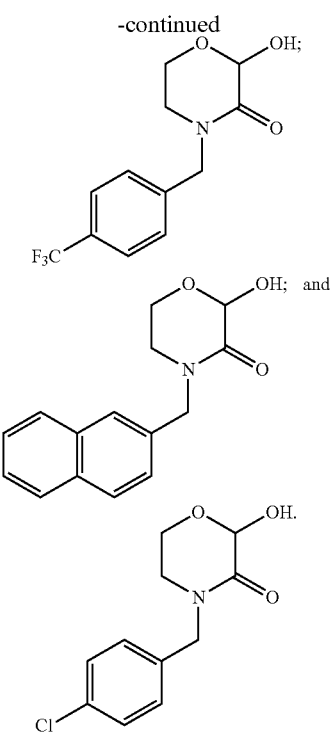

The method for preparing the compound 4-substituent-2-hydroxymorpholin-3-one of Formula I is also encompassed in the present invention, in which the compound of Formula IV as the starting material reacts with the aqueous glyoxalic acid solution to obtain the compound 4-substituent-2-hydroxymorpholin-3-one corresponding to Formula I;

IV

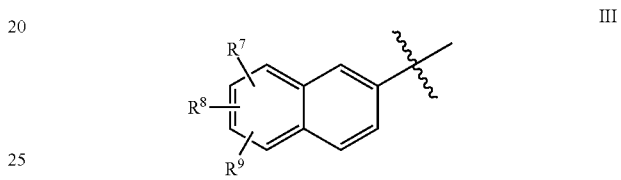

wherein,
G is selected from:
(i) groups of Formula II

II wherein,
$R^1$, $R^2$, and $R^3$ are independently selected from: hydrogen, substituted or unsubstituted $C_1$-$C_6$ alkyl, substituted or unsubstituted $C_2$-$C_6$ alkenyl, $C_2$-$C_6$ alkynyl, substituted or unsubstituted phenyl, halo-, —CN, —$CX_3$ (X is selected from Cl, Br, and F), —$NO_2$, —$SR^6$, —$SOR^6$, —$SO_2R^6$, —$(CH_2)_m$—$NR^4R^5$, —$NR^4COR^5$, —$NR^4CO_2R^5$, —$CONR^4R^5$, —$COR^4$, —$CO_2R^4$, hydroxyl, and $C_1$-$C_6$ alkoxy; the substituents on the $C_1$-$C_6$ alkyl and $C_2$-$C_6$ alkenyl can be independently selected from: hydroxyl, oxo-, $C_1$-$C_6$ alkoxy, phenyl, —CN, —$NO_2$, halo-, —$NR^4R^5$, —$NR^4COR^5$, —$NR^4CO_2R^5$, —$CONR^4R^5$, —$COR^4$, and —$CO_2R^4$; the substituents on the phenyl can be selected from: hydroxyl, $C_1$-$C_6$ alkyl, $C_1$-$C_6$ alkoxy, $C_2$-$C_6$ alkenyl, halo-, —CN, —$NO_2$, —$CF_3$, —$(CH_2)_m$—$NR^4R^5$, —$NR^4COR^5$, —$NR^4CO_2R^5$, —$CONR^4R^5$, —$COR^4$, and —$CO_2R^4$; and $R^1$, $R^2$, and $R^3$ can not be hydrogen at the same time;

$R^4$ and $R^5$ are independently selected from: hydrogen, $C_1$-$C_6$ alkyl, monohydroxyl substituted $C_1$-$C_6$ alkyl, and phenyl;

$R^6$ is hydrogen or $C_1$-$C_6$ alkyl;
m is selected from 1, 2, 3 or 4;
(ii) groups of Formula III

III wherein,
$R^7$, $R^8$, and $R^9$ are independently selected from: hydrogen, substituted or unsubstituted $C_1$-$C_6$ alkyl, substituted or unsubstituted $C_2$-$C_6$ alkenyl, $C_2$-$C_6$ alkynyl, substituted or unsubstituted phenyl, halo-, —CN, —$CX_3$ (X is selected from Cl, Br, and F), —$NO_2$, —$SR^{12}$, —$SOR^{12}$, —$SO_2R^{12}$, —$(CH_2)_m$—$NR^{10}R^{11}$, —$NR^{10}COR^{11}$, —$NR^{10}CO_2R^{11}$, —$CONR^{10}R^{11}$, —$COR^{10}$, —$CO_2R^{10}$, hydroxyl, and $C_1$-$C_6$ alkoxy; the substituents on the $C_1$-$C_6$ alkyl and $C_1$-$C_6$ alkenyl are each independently selected from: hydroxyl, oxo-, $C_1$-$C_6$ alkoxy, phenyl, —CN, —$NO_2$, halo-, —$NR^{10}R^{11}$, —$NR^{10}COR^{11}$, —$NR^{10}CO_2R^{11}$, —$CONR^{10}R^{11}$, —$COR^{10}$, and —$CO_2R^{10}$; the substituents on the phenyl can be selected from: hydroxyl, $C_1$-$C_6$ alkyl, $C_1$-$C_6$ alkoxy, $C_2$-$C_6$ alkenyl, halo-, —CN, —$NO_2$, —$CF_3$, —$(CH_2)_m$—$NR^{10}R^{11}$, —$NR^{10}COR^{11}$, —$NR^{10}CO_2R^{11}$, —$CONR^{10}R^{11}$, —$COR^{10}$, and —$CO_2R^{10}$;

$R^{10}$ and $R^{11}$ are independently selected from: hydrogen, $C_1$-$C_6$ alkyl, monohydroxyl substituted $C_1$-$C_6$ alkyl, and phenyl;

$R^{12}$ is hydrogen or $C_1$-$C_6$ alkyl;
m is selected from 1, 2, 3 or 4.

In this method, the higher the electron-withdrawing effect of $R^1$, $R^2$, and $R^3$ on the groups of Formula II is, the higher the yield of 4-substituent-2-hydroxymorpholin-3-one will be obtained.

The solvent used in the reaction is selected from the group comprising: ethyl acetate, $C_6$-$C_{12}$ alkane, benzene, toluene, paraxylene, chlorobenzene, orthodichlorobenzene, acetone, dichloromethane, chloroform, nitromethane, N,N-dimethyl formamide, dimethyl sulfoxide, 2-butanone, $C_1$-$C_6$ alcohols, 1,3-dioxane, 1,4-dioxane, tetrahydrofuran, acetonitrile, 1,2-dimethyl ethyl, water and the mixture thereof.

Preferably, the solvent used in the reaction can be the solvent miscible with water, including acetone, 2-butanone, N,N-dimethyl formamide, dimethyl sulfoxide, $C_1$-$C_3$ alcohols, 1,3-dioxane, 1,4-dioxane, tetrahydrofuran, acetonitrile, 1,2-dimethyl ethyl and the mixture thereof.

Preferably, the solvent used in the reaction is selected from tetrahydrofuran, acetonitrile and the mixture thereof.

Preferably, the solvent used in the reaction is selected from tetrahydrofuran.

The reaction temperature is selected from 30 to 100° C., and preferably 60 to 70° C.

The aqueous glyoxalic acid solution used in the reaction is selected from the aqueous solution of glyoxalic acid monohydrate, and the aqueous glyoxalic acid solution with a mass ratio of 1-99%, wherein the mass ratio of the aqueous glyoxalic acid solution is preferably 50%.

The present invention also provides a method for preparing the compound of Formula IX, a key intermediate of aprepitant, which is characterized in that the compound of Formula IX can be prepared using the compound of Formula I as the starting material.

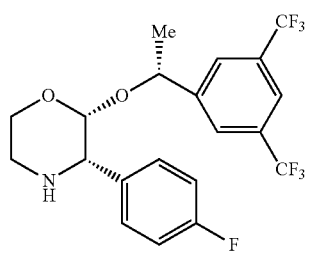

IX

Specific reaction route is as follows:

i) the compound of Formula I is reacted with trifluoroacetic anhydride to obtain the compound of Formula X:

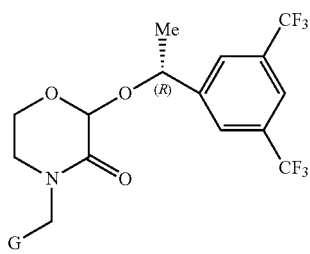

X ii) under the catalysis by boron trifluoride, the compound of Formula X is reacted with the compound of Formula XI,

XI in order to obtain the compound of Formula XII:

XII

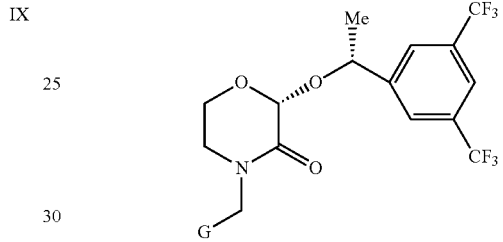

iii) the compound of Formula XII is chirally transformed in the presence of potassium linaloolate to obtain the compound of formula XIII:

XIII iv) after reaction with p-fluorophenyl magnesium bromide, the compound of Formula XIII is hydrogenated under the catalysis by palladium/carbon to obtain the compound of Formula IX.

The reaction equation for preparing the compound of Formula IX from the compound of Formula I is shown below:

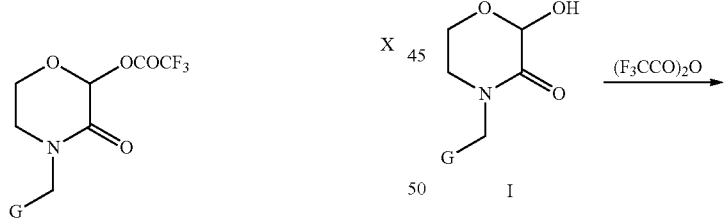

I

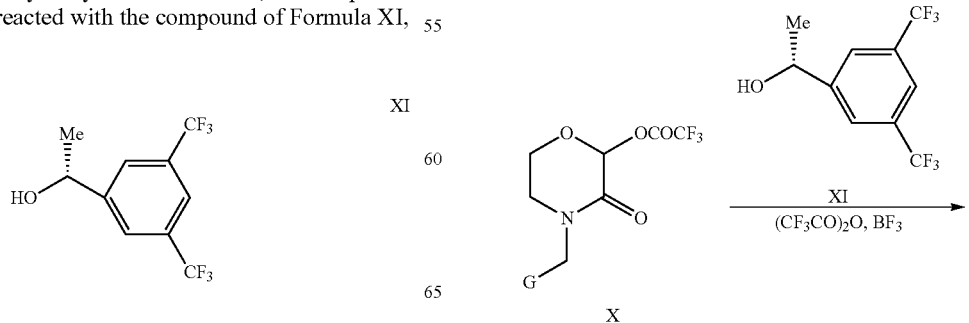

X

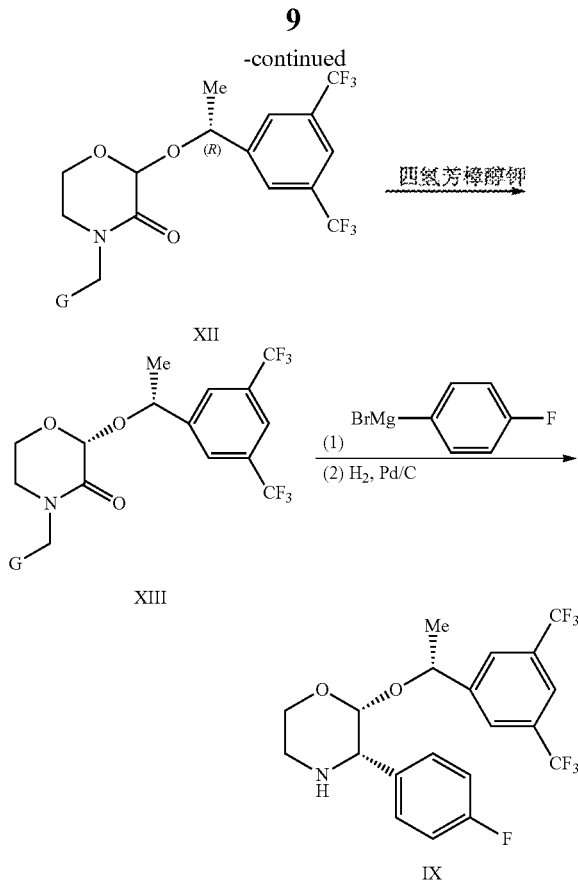

The use of the compound of Formula I in the preparation of aprepitant is also encompassed in the present invention.

In the present invention, when there are electron-withdrawing substituents on the aryl, the reaction yield and time for the preparation of N-substituted-2-hydroxymorpholin-3-one can be significantly improved, as compared with the method reported in J. AM. CHEM. SOC. 2003, 125, 2129-2135. Additionally, the production cost can be significantly reduced for the preparation of aprepitant.

DETAILED EMBODIMENTS

Example 1: The preparation of 2-hydroxy-4-(4-nitrobenzyl)morpholin-3-one 50 wt % aqueous glyoxalic acid solution (46.4 ml, 0.408 mol) (50 wt % referred that the mass ratio of glyoxalic acid is 50%, the same below) and tetrahydrofuran (31 ml) were added into a reaction bottle, and heated up to reflux. Subsequently, 2-(4-nitrobenzylamino)ethanol (40 g, 0.204 mol) in tetrahydrofuran (71 ml) was slowly added dropwise. After the addition, it was refluxed for 8 h. Water (102 ml) is then added. The tetrahydrofuran was removed by evaporation under reduced pressure. The residue was heated until dissolved, and it was then cooled down for crystallization to give 2-hydroxy-4-(4-nitrobenzyl)morpholin-3-one (47.2 g, 91.7%) as a light yellow solid;

TOF-MS (m/z): 253.1 [M+1];

$^1$H-NMR (400 MHz, CDCl$_3$) δ: 8.21 (d, J=8.8, 2H), 7.52 (d, J=8.8, 2H), 7.11 (d, J=6.4, 1H), 5.06 (d, J=6.4, 1H), 4.65 (dd, J=43.6, 15.6, 2H), 4.15 (ddd, J=11.6, 11.2, 3.6, 1H), 3.73 (ddd, J=12.0, 4.4, 2.0, 1H), 3.43 (ddd, J=14.8, 12.0, 4.8, 1H), 3.19 (ddd, J=10.8, 3.6, 1.6, 1H).

Example 2: The preparation of 2-hydroxy-4-(3-nitrobenzyl)morpholin-3-one 50 wt % aqueous glyoxalic acid solution (46.4 ml, 0.408 mol) and tetrahydrofuran (31 ml) were added into a reaction bottle, and heated up to reflux. Subsequently, 2-(3-nitrobenzylamino)ethanol (40 g, 0.204 mol) in tetrahydrofuran (71 ml) was slowly added dropwise. After the addition, it was refluxed for 8 h. Water (102 ml) is then added. The tetrahydrofuran was removed by evaporation under reduced pressure. The residue was heated until dissolved, and it was then cooled down for crystallization to give 2-hydroxy-4-(3-nitrobenzyl)morpholin-3-one (46.5 g, 90.3%) as a light yellow solid;

TOF-MS (m/z): 253.1 [M+1];

$^1$H-NMR (400 MHz, CDCl$_3$) δ: 8.11 (d, m, 2H), 7.75 (d, m, 2H), 7.18 (d, J=6.4, 1H), 5.10 (d, J=6.4, 1H), 4.55 (dd, J=65.6, 15.6, 2H), 4.21 (ddd, J=12.0, 11.0, 3.6, 1H), 3.79 (ddd, J=12.0, 4.6, 2.0, 1H), 3.46 (ddd, J=16.0, 12.0, 4.8, 1H), 3.22 (ddd, J=11.2, 3.6, 1.6, 1H).

Example 3: The preparation of 2-hydroxy-4-(2-nitrobenzyl)morpholin-3-one 50 wt % aqueous glyoxalic acid solution (46.4 ml, 0.408 mol) and tetrahydrofuran (31 ml) were added into a reaction bottle, and heated up to reflux. Subsequently, 2-(2-nitrobenzylamino)ethanol (40 g, 0.204 mol) in tetrahydrofuran (71 ml) was slowly added dropwise. After the addition, it was refluxed for 8 h. Water (102 ml) is then added. The tetrahydrofuran was removed by evaporation under reduced pressure. The residue was heated until dissolved, and it was then cooled down for crystallization to give 2-hydroxy-4-(2-nitrobenzyl)morpholin-3-one (46.1 g, 89.5%) as a light yellow solid;

TOF-MS (m/z): 253.1 [M+1];

$^1$H-NMR (400 MHz, CDCl$_3$) δ: 8.06 (dd, J=8.0, 1.2, 1H), 7.76 (ddd, J=8.0, 7.2, 0.8, 1H), 7.56 (ddd, J=8.4, 7.2, 0.4, 1H), 7.38 (d, J=8.0, 1H), 7.15 (d, J=6.4, 1H), 5.08 (d, J=6.0, 1H), 4.82 (dd, J=71.2, 15.6, 2H), 4.20 (ddd, J=15.2, 7.6, 4.0, 1H), 3.76 (ddd, J=9.6, 7.2, 2.4, 1H), 3.47 (ddd, J=12.0, 10.8, 4.8, 1H), 3.21 (ddd, J=12.4, 3.6, 2.4, 1H).

Example 4: The preparation of 2-hydroxy-4-(2-chlorobenzyl)morpholin-3-one 50 wt % aqueous glyoxalic acid solution (49.1 ml, 0.431 mol) and tetrahydrofuran (32 ml) were added into a reaction bottle, and heated up to reflux. Subsequently, 2-(2-chlorobenzylamino)ethanol (40 g, 0.215 mol) in tetrahydrofuran (76 ml) was slowly added dropwise. After the addition, it was refluxed for 8 h. Water (108 ml) is then added. The tetrahydrofuran was removed by evaporation under reduced pressure. The residue was heated until dissolved, and it was then cooled down for crystallization to give 2-hydroxy-4-(2-chlorobenzyl)morpholin-3-one (41.2 g, 78.9%) as a white solid;

TOF-MS (m/z): 242.2 [M+1];

$^1$H-NMR (400 MHz, CDCl$_3$) δ: 7.47 (dd, J=7.6, 1.6, 1H), 7.35 (ddd, 14.4, 7.6, 5.6, 2H), 7.25 (m, 1H), 7.09 (d, J=6.4, 1H), 5.07 (d, J=6.4, 1H), 4.60 (dd, J=42.8, 16.0, 2H), 4.18 (ddd, J=14.8, 11.2, 3.6, 1H), 3.74 (ddd, J=12.0, 4.8, 2.0, 1H), 3.42 (ddd, J=15.2, 10.4, 4.4, 1H), 3.17 (ddd, J=12.4, 4.0, 2.4, 1H).

Example 5: The preparation of 2-hydroxy-4-(3-chlorobenzyl)morpholin-3-one 50 wt % aqueous glyoxalic acid solution (49.1 ml, 0.431 mol) and tetrahydrofuran (32 ml) were added into a reaction bottle, and heated up to reflux. Subsequently, 2-(3-chlorobenzylamino)ethanol (40 g, 0.215 mol) in tetrahydrofuran (75 ml) was slowly added dropwise. After the addition, it was refluxed for 12 h. Water (108 ml) is then added. The tetrahydrofuran was removed by evaporation under reduced pressure. The residue was heated until dissolved, and it was then cooled down for crystallization to give 2-hydroxy-4-(3-chlorobenzyl)morpholin-3-one (40.2 g, 76.9%) as a white solid;

TOF-MS (m/z): 242.2 [M+1];
$^1$H-NMR (400 MHz, CDCl$_3$) δ: 7.51 (m, 2H), 7.33 (m, 2H), 7.12 (d, J=6.2, 1H), 5.08 (d, J=6.2, 1H), 4.54 (dd, J=44.0, 12.2, 2H), 4.14 (ddd, J=16.0, 11.6, 4.0, 1H), 3.69 (ddd, J=12.4, 4.8, 2.4, 1H), 3.38 (ddd, J=12.8, 11.0, 4.8, 1H), 3.20 (ddd, J=12.4, 3.6, 2.4, 1H);

Example 6: The preparation of 2-hydroxy-4-(4-chlorobenzyl)morpholin-3-one 50 wt % aqueous glyoxalic acid solution (49.1 ml, 0.431 mol) and tetrahydrofuran (32 ml) were added into a reaction bottle, and heated up to reflux. Subsequently, 2-(4-chlorobenzylamino)ethanol (40 g, 0.215 mol) in tetrahydrofuran (75 ml) was slowly added dropwise. After the addition, it was refluxed for 12 h. Water (108 ml) is then added. The tetrahydrofuran was removed by evaporation under reduced pressure. The residue was heated until dissolved, and it was then cooled down for crystallization to give 2-hydroxy-4-(4-chlorobenzyl)morpholin-3-one (40.8 g, 78.1%) as a white solid;

TOF-MS (m/z): 242.2 [M+1];
$^1$H-NMR (400 MHz, CDCl$_3$) δ: 7.34 (dd, J=60.8, 8.0, 4H), 7.06 (d, J=6.0, 1H), 5.04 (d, J=6.0, 1H), 4.50 (dd, J=52.0, 15.2, 2H), 4.11 (ddd, J=15.6, 11.2, 4.0, 1H), 3.69 (ddd, J=12.0, 4.8, 2.0, 1H), 3.36 (ddd, J=12.4, 10.8, 4.8, 1H), 3.17 (ddd, J=12.8, 3.6, 2.4, 1H).

Example 7: The preparation of 2-hydroxy-4-(2,4-dichlorobenzyl)morpholin-3-one 50 wt % aqueous glyoxalic acid solution (41.3 ml, 0.363 mol) and tetrahydrofuran (27 ml) were added into a reaction bottle, and heated up to reflux. Subsequently, 2-(2,4-dichlorobenzylamino)ethanol (40 g, 0.182 mol) in tetrahydrofuran (64 ml) was slowly added dropwise. After the addition, it was refluxed for 8 h. Water (91 ml) is then added. The tetrahydrofuran was removed by evaporation under reduced pressure. The residue was heated until dissolved, and it was then cooled down for crystallization to give 2-hydroxy-4-(2,4-dichlorobenzyl)morpholin-3-one (41.4 g, 82.4%) as a white solid;

TOF-MS (m/z): 276.2 [M+1];
$^1$H-NMR (400 MHz, CDCl$_3$) δ: 7.63 (d, J=2.4, 1H), 7.45 (dd, J=8.4, 2.0, 1H), 7.27 (d, J=8.4, 1H), 7.11 (d, J=6.4, 1H), 5.06 (d, J=5.6, 1H), 4.57 (dd, J=47.2, 15.6, 2H), 4.17 (ddd, J=15.6, 10.8, 3.6, 1H), 3.73 (ddd, J=12.0, 4.8, 2.0, 1H), 3.42 (ddd, J=15.6 10.8, 4.8, 1H), 3.18 (ddd, J=12.4, 4.0, 2.4, 1H).

Example 8: The Preparation of 2-hydroxy-4-(4-trifluoromethylbenzyl)morpholin-3-one 50 wt % aqueous glyoxalic acid solution (41.5 ml, 0.364 mol) and tetrahydrofuran (27 ml) were added into a reaction bottle, and heated up to reflux. Subsequently, 2-(4-trifluoromethylbenzylamino)ethanol (40 g, 0.182 mol) in tetrahydrofuran (64 ml) was slowly added dropwise. After the addition, it was refluxed for 8 h. After the reaction was finished, water (91 ml) is then added. The tetrahydrofuran was removed by evaporation under reduced pressure. The residue was heated until dissolved, and it was then cooled down for crystallization to give 2-hydroxy-4-(4-trifluoromethylbenzyl)morpholin-3-one (47.8 g, 75.2%) as a white solid;

TOF-MS (m/z): 276.0 [M+1];
$^1$H-NMR (400 MHz, CDCl$_3$) δ: 7.71 (d, J=8.8, 1H), 7.47 (d, J=8.0, 1H), 7.07 (d, J=6.4, 1H), 5.06 (d, J=6.4, 1H), 4.60 (dd, J=41.6, 15.2, 2H), 4.14 (ddd, J=15.6, 10.8, 3.6, 1H), 3.71 (ddd, J=12.0, 4.8, 2.4, 1H), 3.40 (ddd, J=15.6 10.8, 4.8, 1H), 3.26 (ddd, J=12.8, 4.0, 2.4, 1H).

Example 9: The Preparation of 2-hydroxy-4-(3-trifluoromethylbenzyl)morpholin-3-one 50 wt % aqueous glyoxalic acid solution (41.5 ml, 0.364 mol) and tetrahydrofuran (27 ml) were added into a reaction bottle, and heated up to reflux. Subsequently, 2-(3-trifluoromethylbenzylamino)ethanol (40 g, 0.182 mol) in tetrahydrofuran (64 ml) was slowly added dropwise. After the addition, it was refluxed for 8 h. After the reaction was finished, water (91 ml) is then added. The tetrahydrofuran was removed by evaporation under reduced pressure. The residue was heated until dissolved, and it was then cooled down for crystallization to give 2-hydroxy-4-(3-trifluoromethylbenzyl)morpholin-3-one (48.6 g, 76.8%) as a white solid;

TOF-MS (m/z): 276.0 [M+1];
$^1$H-NMR (400 MHz, CDCl$_3$) δ: 7.80 (m, 2H), 7.51 (m, 2H), 7.10 (d, J=6.4, 1H), 5.12 (d, J=6.4, 1H), 4.62 (dd, J=54.6, 15.2, 2H), 4.16 (ddd, J=15.8, 11.2, 3.6, 1H), 3.74 (ddd, J=12.2, 4.8, 2.4, 1H), 3.44 (ddd, J=15.8, 11.0, 4.8, 1H), 3.28 (ddd, J=12.8, 4.4, 2.4, 1H).

Example 10: The Preparation of 2-hydroxy-4-(2-trifluoromethylbenzyl)morpholin-3-one 50 wt % aqueous glyoxalic acid solution (41.5 ml, 0.364 mol) and tetrahydrofuran (27 ml) were added into a reaction bottle, and heated up to reflux. Subsequently, 2-(2-trifluoromethylbenzylamino)ethanol (40 g, 0.182 mol) in tetrahydrofuran (64 ml) was slowly added dropwise. After the addition, it was refluxed for 8 h. After the reaction was finished, water (91 ml) is then added. The tetrahydrofuran was removed by evaporation under reduced pressure. The residue was heated until dissolved, and it was then cooled down for crystallization to give 2-hydroxy-4-(2-trifluoromethylbenzyl)morpholin-3-one (52.3 g, 82.9%) as a white solid;

TOF-MS (m/z): 276.0 [M+1];
$^1$H-NMR (400 MHz, CDCl$_3$) δ: 7.96 (m, 2H), 7.72 (m, 2H), 7.21 (d, J=6.4, 1H), 5.34 (d, J=6.4, 1H), 4.62 (dd, J=64.2, 14.4, 2H), 4.16 (ddd, J=16.2, 11.0, 4.4, 1H), 3.74 (ddd, J=12.4, 4.6, 2.4, 1H), 3.44 (ddd, J=15.8, 11.0, 4.8, 1H), 3.28 (ddd, J=12.6, 4.6, 2.4, 1H).

Example 11: The preparation of 2-hydroxy-4-(4-naphth-2-ylmethyl)morpholin-3-one 50 wt % aqueous glyoxalic acid solution (45.3 ml, 0.398 mol) and tetrahydrofuran (30 ml) were added into a reaction bottle, and heated up to reflux. Subsequently, 2-(naphth-2-ylmethylamino)ethanol (40 g, 0.199 mol) in tetrahydrofuran (70 ml) was slowly added dropwise. After the addition, it was refluxed for 24 h. Water (100 ml) is then added. The tetrahydrofuran is removed by evaporation under reduced pressure. The residue was heated until dissolved, and it was then cooled down for crystallization to give 2-hydroxy-4-(4-naphth-2-ylmethyl)morpholin-3-one (40.3 g, 78.8%) as a white solid;

TOF-MS (m/z): 258.1 [M+1];
$^1$H-NMR (400 MHz, CDCl$_3$) δ: 7.84 (m, 3H), 7.54 (s, 1H), 7.50 (m, 2H), 7.40 (dd, J=8.4, 1.6, 1H), 7.07 (d, J=6.0, 1H), 5.06 (d, J=5.6, 1H), 4.69 (dd, J=31.6, 14.8, 2H), 4.13 (ddd, J=13.5, 9.3, 3.6, 1H), 3.70 (ddd, J=12.0, 4.8, 2.0, 1H), 3.39 (ddd, J=15.6 10.4, 4.8, 1H), 3.26 (ddd, J=12.0, 3.6, 2.4, 1H).

Example 12: The preparation of 2-hydroxy-4-(3-cyanobenzyl)morpholin-3-one 50 wt % aqueous glyoxalic acid solution (51.7 ml, 0.454 mol) and tetrahydrofuran (34 ml) were added into a reaction bottle, and heated up to reflux. Subsequently, 2-(3-cyanobenzylamino)ethanol (40 g, 0.227 mol) in tetrahydrofuran (79 ml) was slowly added dropwise. After the addition, it was refluxed for 12 h. Water (113 ml) is then added. The tetrahydrofuran is removed by evaporation under reduced pressure. The residue was heated until dissolved, and it was then cooled down for crystallization to give 2-hydroxy-4-(3-cyanobenzyl)morpholin-3-one (37.6 g, 71.4%) as a white solid;

TOF-MS (m/z): 233.1 [M+1];
$^1$H-NMR (400 MHz, CDCl$_3$) δ: 7.88 (m, 2H), 7.50 (m, 2H), 7.22 (d, J=8.4, 1H), 5.12 (d, J=6.4, 1H), 4.62 (dd, J=68.8, 15.2, 2H), 4.24 (ddd, J=12.0, 11.2, 4.0, 1H), 3.78 (ddd, J=12.4, 4.8, 2.0, 1H), 3.51 (ddd, J=12.6, 10.6, 4.8, 1H), 3.22 (ddd, J=12.8, 3.6, 2.4, 1H).

Example 13: The preparation of 2-hydroxy-4-(2-cyanobenzyl)morpholin-3-one 50 wt % aqueous glyoxalic acid solution (51.7 ml, 0.454 mol) and tetrahydrofuran (34 ml) were added into a reaction bottle, and heated up to reflux. Subsequently, 2-(2-cyanobenzylamino)ethanol (40 g, 0.227 mol) in tetrahydrofuran (79 ml) was slowly added dropwise. After the addition, it was refluxed for 12 h. Water (113 ml) is then added. The tetrahydrofuran is removed by evaporation under reduced pressure. The residue was heated until dissolved, and it was then cooled down for crystallization to give 2-hydroxy-4-(2-cyanobenzyl)morpholin-3-one (39.9 g, 75.8%) as a white solid;

TOF-MS (m/z): 233.1 [M+1];
$^1$H-NMR (400 MHz, CDCl$_3$) δ: 8.02 (m, 2H), 7.72 (m, 2H), 7.36 (d, J=8.6, 1H), 5.22 (d, J=6.8, 1H), 4.74 (dd, J=72.6, 15.8, 2H), 4.36 (ddd, J=12.4, 11.4, 4.0, 1H), 3.94 (ddd, J=12.0, 4.6, 2.0, 1H), 3.69 (ddd, J=12.4, 10.6, 4.2, 1H), 3.31 (ddd, J=12.6, 3.4, 2.4, 1H).

Example 14: The preparation of 2-hydroxy-4-(4-methylbenzyl)morpholin-3-one 50 wt % aqueous glyoxalic acid solution (55.1 ml, 0.484 mol) and tetrahydrofuran (36 ml) were added into a reaction bottle, and heated up to reflux. Subsequently, 2-(4-methylbenzylamino)ethanol (40 g, 0.242 mol) in tetrahydrofuran (85 ml) was slowly added dropwise. After the addition, it was refluxed for 18 h. Water (121 ml) is then added. The tetrahydrofuran is removed by evaporation under reduced pressure. The residue was heated until dissolved, and it was then cooled down for crystallization to give 2-hydroxy-4-(4-methylbenzyl)morpholin-3-one (31.2 g, 58.3%) as a white solid;

TOF-MS (m/z): 222.1 [M+1];
$^1$H-NMR (400 MHz, CDCl3) δ: 7.13 (dd, J=19.6, 8.4, 4H), 7.02 (s, 1H), 5.03 (s, 1H), 4.47 (dd, J=44.0, 14.4, 2H), 4.08 (ddd, J=12.0, 11.6, 4.0, 1H), 3.68 (ddd, J=9.6, 4.8, 2.4, 1H), 3.30 (ddd, J=12.4, 10.8, 5.2, 1H), 3.08 (ddd, J=10.4, 3.6, 2.0, 1H).

Example 15: The preparation of 2-hydroxy-4-(4-methoxylbenzyl)morpholin-3-one 50 wt % aqueous glyoxalic acid solution (50.3 ml, 0.442 mol) and tetrahydrofuran (33 ml) were added into a reaction bottle, and heated up to reflux. Subsequently, 2-(4-methoxylbenzylamino)ethanol (40 g, 0.221 mol) in tetrahydrofuran (78 ml) was slowly added dropwise. After the addition, it was refluxed for 18 h. Water (100 ml) is then added. The tetrahydrofuran is removed by evaporation under reduced pressure. The residue was heated until dissolved, and it was then cooled down for crystallization to give 2-hydroxy-4-(4-methoxylbenzyl)morpholin-3-one (23.4 g, 44.7%) as a white solid;

TOF-MS (m/z): 238.1 [M+1];
$^1$H-NMR (400 MHz, CDCl$_3$) δ: 7.18 (d, J=8.8, 2H), 7.06 (d, J=1.6, 1H), 6.90 (d, J=8.8, 2H), 5.01 (d, J=6.4, 1H), 4.43 (dd, J=22.8, 14.4, 2H), 4.06 (ddd, J=11.6, 11.2, 4.0, 1H), 3.73 (s, 3H), 3.67 (ddd, J=12.0, 4.8, 2.0, 1H), 3.30 (ddd, J=12.4, 11.2, 4.8, 1H), 3.08 (ddd, J=12.4, 3.6, 2.0, 1H).

Example 16: The preparation of 2-hydroxy-4-(2-methoxylbenzyl)morpholin-3-one 50 wt % aqueous glyoxalic acid solution (50.3 ml, 0.442 mol) and tetrahydrofuran (33 ml) were added into a reaction bottle, and heated up to reflux. Subsequently, 2-(2-methoxylbenzylamino)ethanol (40 g, 0.221 mol) in tetrahydrofuran (78 ml) was slowly added dropwise. After the addition, it was refluxed for 18 h. Water (100 ml) is then added. The tetrahydrofuran is removed by evaporation under reduced pressure. The residue was heated until dissolved, and it was then cooled down for crystallization to give 2-hydroxy-4-(2-methoxylbenzyl)morpholin-3-one (14.3 g, 27.2%) as a white solid;

TOF-MS (m/z): 238.1 [M+1];
$^1$H-NMR (400 MHz, CDCl$_3$) δ: 7.25 (m, 1H), 7.07 (d, J=7.6, 1H), 6.99 (d, J=8.0, 1H), 6.91 (t, J=7.6, 1H), 5.01 (s, 1H), 4.43 (dd, J=38.8, 15.2, 2H), 4.10 (ddd, J=11.6, 11.2, 4.0, 1H), 3.77 (s, 3H), 3.67 (ddd, J=12.0, 3.6, 2.0, 1H), 3.36 (ddd, J=12.8, 10.4, 5.2, 1H), 3.12 (ddd, J=10.0, 6.0 2.4, 1H).

Example 17: The preparation of 2-hydroxy-4-(3-methylbenzyl)morpholin-3-one 50 wt % aqueous glyoxalic acid solution (55.1 ml, 0.484 mol) and tetrahydrofuran (36 ml) were added into a reaction bottle, and heated up to reflux. Subsequently, 2-(3-methylbenzylamino)ethanol (40 g, 0.242 mol) in tetrahydrofuran (85 ml) was slowly added dropwise. After the addition, it was refluxed for 24 h. Water (121 ml) is then added. The tetrahydrofuran is removed by evaporation under reduced pressure. The residue was heated until dissolved, and it was then cooled down for crystallization to give 2-hydroxy-4-(3-methylbenzyl)morpholin-3-one (10.3 g, 19.3%) as a white solid;

TOF-MS (m/z): 222.1 [M+1];

¹H-NMR (400 MHz, CDCl₃) δ: 7.24 (m, 2H), 7.02 (m, 1H), 5.33 (s, 1H), 4.57 (dd, J=80.4, 14.8, 2H), 4.23 (ddd, J=14.0, 10.4, 4.0, 1H), 4.12 (s, 1H), 3.67 (ddd, J=11.6, 4.4, 3.2, 1H), 3.42 (ddd, J=12.4, 10.4, 4.4, 1H), 3.27 (s, 1H), 3.08 (ddd, J=10.8, 4.8, 3.6, 1H).

Example 18: The preparation of 2-hydroxy-4-(2,4-dimethoxybenzyl)morpholin-3-one 50 wt % aqueous glyoxalic acid solution (43.1 ml, 0.379 mol) and tetrahydrofuran (28 ml) were added into a reaction bottle, and heated up to reflux. Subsequently, 2-(2,4-dimethoxybenzylamino)ethanol (40 g, 0.189 mol) in tetrahydrofuran (67 ml) was slowly added dropwise. After the addition, it was refluxed for 24 h. Water (95 ml) is then added. The tetrahydrofuran is removed by evaporation under reduced pressure. The residue was heated until dissolved, and it was then cooled down for crystallization to give 2-hydroxy-4-(2,4-dimethoxybenzyl)morpholin-3-one (9.75 g, 19.3%) as a white solid;

TOF-MS (m/z): 268.1 [M+1];

¹H-NMR (400 MHz, CDCl₃) δ: 7.19 (d, J=8.8, 1H), 6.46 (m, 2H), 5.25 (d, J=2.8, 1H), 4.57 (dd, J=30.8, 14.0, 2H), 4.18 (ddd, J=14.0, 10.0, 4.0, 1H), 3.80 (s, 6H), 3.67 (ddd, J=10.8, 6.2, 4.0, 1H), 3.42 (ddd, J=12.8, 9.6, 4.4, 1H), 3.19 (ddd, J=10.0, 6.0, 4.0, 1H).

Example 19: The preparation of 2-hydroxy-4-(4-nitrobenzyl)morpholin-3-one 10 wt % aqueous glyoxalic acid solution (232.0 ml, 0.408 mol) and tetrahydrofuran (31 ml) were added into a reaction bottle, and heated up to reflux. Subsequently, 2-(4-nitrobenzylamino)ethanol (40 g, 0.204 mol) in tetrahydrofuran (71 ml) was slowly added dropwise. After the addition, it was refluxed for 8 h. Water (102 ml) is then added. The tetrahydrofuran is removed by evaporation under reduced pressure. The residue was heated until dissolved, and it was then cooled down for crystallization to give 2-hydroxy-4-(4-nitrobenzyl)morpholin-3-one (40.3 g, 78.3%) as a light yellow solid.

TOF-MS (m/z): 253.1 [M+1];

¹H-NMR (400 MHz, CDCl₃) δ: 8.22 (d, J=8.8, 2H), 7.51 (d, J=8.8, 2H), 7.11 (d, J=6.4, 1H), 5.08 (d, J=6.4, 1H), 4.65 (dd, J=43.6, 15.6, 2H), 4.15 (ddd, J=11.6, 11.2, 3.6, 1H), 3.72 (ddd, J=12.0, 4.4, 2.0, 1H), 3.42 (ddd, J=14.8, 12.0, 4.8, 1H), 3.19 (ddd, J=10.8, 3.6, 1.6, 1H).

Example 20: The preparation of 2-hydroxy-4-(4-nitrobenzyl)morpholin-3-one 30 wt % aqueous glyoxalic acid solution (77.3 ml, 0.408 mol) and tetrahydrofuran (31 ml) were added into a reaction bottle, and heated up to reflux. Subsequently, 2-(4-nitrobenzylamino)ethanol (40 g, 0.204 mol) in tetrahydrofuran (71 ml) was slowly added dropwise. After the addition, it was refluxed for 8 h. Water (102 ml) is then added. The tetrahydrofuran is removed by evaporation under reduced pressure. The residue was heated until dissolved, and it was then cooled down for crystallization to give 2-hydroxy-4-(4-nitrobenzyl)morpholin-3-one (43.0 g, 83.6%) as a light yellow solid.

TOF-MS (m/z): 253.1 [M+1];

¹H-NMR (400 MHz, CDCl₃) δ: 8.20 (d, J=8.8, 2H), 7.51 (d, J=8.8, 2H), 7.11 (d, J=6.4, 1H), 5.08 (d, J=6.4, 1H), 4.66 (dd, J=43.6, 15.6, 2H), 4.15 (ddd, J=11.6, 11.2, 3.6, 1H), 3.70 (ddd, J=12.0, 4.4, 2.0, 1H), 3.40 (ddd, J=14.8, 12.0, 4.8, 1H), 3.20 (ddd, J=10.8, 3.6, 1.6, 1H).

Example 21: The preparation of 2-hydroxy-4-(4-nitrobenzyl)morpholin-3-one 70 wt % aqueous glyoxalic acid solution (33.1 ml, 0.408 mol) and tetrahydrofuran (31 ml) were added into a reaction bottle, and heated up to reflux. Subsequently, 2-(4-nitrobenzylamino)ethanol (40 g, 0.204 mol) in tetrahydrofuran (71 ml) was slowly added dropwise. After the addition, it was refluxed for 8 h. Water (102 ml) is then added. The tetrahydrofuran is removed by evaporation under reduced pressure. The residue was heated until dissolved, and it was then cooled down for crystallization to give 2-hydroxy-4-(4-nitrobenzyl)morpholin-3-one (41.5 g, 80.7%) as a light yellow solid.

TOF-MS (m/z): 253.1 [M+1];

¹H-NMR (400 MHz, CDCl₃) δ: 8.21 (d, J=8.8, 2H), 7.52 (d, J=8.8, 2H), 7.13 (d, J=6.4, 1H), 5.08 (d, J=6.4, 1H), 4.65 (dd, J=43.8, 15.6, 2H), 4.17 (ddd, J=11.6, 11.2, 3.6, 1H), 3.72 (ddd, J=12.0, 4.4, 2.0, 1H), 3.42 (ddd, J=14.6, 12.0, 4.8, 1H), 3.17 (ddd, J=10.8, 3.6, 1.6, 1H).

Example 22: The preparation of 2-hydroxy-4-(4-nitrobenzyl)morpholin-3-one 90 wt % aqueous glyoxalic acid solution (25.8 ml, 0.408 mol) and tetrahydrofuran (31 ml) were added into a reaction bottle, and heated up to reflux. Subsequently, 2-(4-nitrobenzylamino)ethanol (40 g, 0.204 mol) in tetrahydrofuran (71 ml) was slowly added dropwise. After the addition, it was refluxed for 8 h. Water (102 ml) is then added. The tetrahydrofuran is removed by evaporation under reduced pressure. The residue was heated until dissolved, and it was then cooled down for crystallization to give 2-hydroxy-4-(4-nitrobenzyl)morpholin-3-one (37.8 g, 73.4%) as a light yellow solid.

TOF-MS (m/z): 253.1 [M+1];

¹H-NMR (400 MHz, CDCl₃) δ: 8.20 (d, J=8.6, 2H), 7.51 (d, J=8.8, 2H), 7.14 (d, J=6.4, 1H), 5.08 (d, J=6.4, 1H), 4.66 (dd, J=43.6, 15.6, 2H), 4.14 (ddd, J=11.6, 11.2, 3.6, 1H), 3.72 (ddd, J=12.0, 4.4, 2.0, 1H), 3.42 (ddd, J=14.8, 12.0, 4.8, 1H), 3.19 (ddd, J=10.8, 3.6, 1.6, 1H).

The invention claimed is:

1. A compound of Formula I:

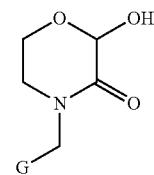

wherein,

G is selected from the group consisting of:

(i) groups of Formula II

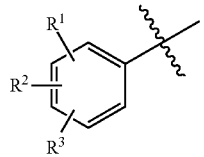

II wherein, $R^1$ is hydrogen, substituted or unsubstituted $C_1$-$C_6$ alkyl, substituted or unsubstituted $C_2$-$C_6$ alkenyl, $C_2$-$C_6$ alkynyl, substituted or unsubstituted phenyl, chloro, bromo, iodo, —CN, —CX$_3$, —NO$_2$, —SR$^6$, —SOR$^6$, —SO$_2$R$^6$, —(CH$_2$)$_m$—NR$^4$R$^5$, —NR$^4$COR$^5$, —NR$^4$CO$_2$R$^5$, —CONR$^4$R$^5$, —COR$^4$, —CO$_2$R$^4$, or hydroxyl;

$R^2$ is hydrogen, substituted or unsubstituted $C_1$-$C_6$ alkyl, substituted or unsubstituted $C_2$-$C_6$ alkenyl, $C_2$-$C_6$ alkynyl, substituted or unsubstituted phenyl, halo, —CN, —CX$_3$, —NO$_2$, —SR$^6$, —SOR$^6$, —SO$_2$R$^6$, —(CH$_2$)$_m$—NR$^4$R$^5$, —NR$^4$COR$^5$, —NR$^4$CO$_2$R$^5$, —CONR$^4$R$^5$, —COR$^4$, —CO$_2$R$^4$, or hydroxyl;

$R^3$ is hydrogen, substituted or unsubstituted $C_1$-$C_6$ alkyl, substituted or unsubstituted $C_2$-$C_6$ alkenyl, $C_2$-$C_6$ alkynyl, substituted or unsubstituted phenyl, halo, —CN, —CX$_3$, —NO$_2$, —SR$^6$, —SOR$^6$, —SO$_2$R$^6$, —(CH$_2$)$_m$—NR$^4$R$^5$, —NR$^4$COR$^5$, —NR$^4$CO$_2$R$^5$, —CONR$^4$R$^5$, —COR$^4$, —CO$_2$R$^4$, or hydroxyl;

when the $C_1$-$C_6$ alkyl or $C_2$-$C_6$ alkenyl of $R^1$, $R^2$, or $R^3$ is substituted, the substituent is, or the substituents are independently, selected from the group consisting of: hydroxyl, oxo-, $C_1$-$C_6$ alkoxy, phenyl, —CN, —NO$_2$, halo, —NR$^4$R$^5$, —NR$^4$COR$^5$, —NR$^4$CO$_2$R$^5$, —CONR$^4$R$^5$, —COR$^4$, and —CO$_2$R$^4$;

when the phenyl of $R^1$, $R^2$, or $R^3$ is substituted, the substituent is, or the substituents are independently, selected from the group consisting of: hydroxyl, $C_1$-$C_6$ alkyl, $C_1$-$C_6$ alkoxy, $C_2$-$C_6$ alkenyl, halo, —CN, —NO$_2$, —CF$_3$, —(CH$_2$)$_m$—NR$^4$R$^5$, —NR$^4$COR$^5$, —NR$^4$CO$_2$R$^5$, —CONR$^4$R$^5$, —COR$^4$, and —CO$_2$R$^4$;

provided that $R^1$, $R^2$, and $R^3$ are not hydrogen at the same time;

$R^4$ and $R^5$ are independently selected from the group consisting of: hydrogen, $C_1$-$C_6$ alkyl, monohydroxyl substituted $C_1$-$C_6$ alkyl, and phenyl;

$R^6$ is hydrogen or $C_1$-$C_6$ alkyl;

X is selected from the group consisting of Cl, Br, and F; and m is 1, 2, 3 or 4; and (ii) groups of Formula III

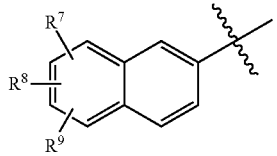

III wherein, $R^7$, $R^8$, and $R^9$ are independently hydrogen, substituted or unsubstituted $C_1$-$C_6$ alkyl, substituted or unsubstituted $C_2$-$C_6$ alkenyl, $C_2$-$C_6$ alkynyl, substituted or unsubstituted phenyl, halo, —CN, —CX$_3$, —NO$_2$, —SR$^{12}$, —SOR$^{12}$, —SO$_2$R$^{12}$, —(CH$_2$)$_m$—NR$^{10}$R$^{11}$, —NR$^{10}$COR$^{11}$, —NR$^{10}$CO$_2$R$^{11}$, —CONR$^{10}$R$^{11}$, —COR$^{10}$, —CO$_2$R$^{10}$, hydroxyl, or $C_1$-$C_6$ alkoxy;

when the $C_1$-$C_6$ alkyl or $C_2$-$C_6$ alkenyl of $R^7$, $R^8$, or $R^9$ is substituted, the substituent is, or the substituents are independently, selected from the group consisting of: hydroxyl, oxo-, $C_1$-$C_6$ alkoxy, phenyl, —CN, —NO$_2$, halo, —NR$^{10}$R$^{11}$, —NR$^{10}$COR$^{11}$, —NR$^{10}$CO$_2$R$^{11}$, —CONR$^{10}$R$^{11}$, —COR$^{10}$, and —CO$_2$R$^{10}$;

when the phenyl of $R^7$, $R^8$, or $R^9$ is substituted, the substituent is, or the substituents are independently, selected from the group consisting of: hydroxyl, $C_1$-$C_6$ alkyl, $C_1$-$C_6$ alkoxy, $C_2$-$C_6$ alkenyl, halo, —CN, —NO$_2$, —CF$_3$, —(CH$_2$)$_m$—NR$^{10}$R$^{11}$, —NR$^{10}$COR$^{11}$, —NR$^{10}$CO$_2$R$^{11}$, —CONR$^{10}$R$^{11}$, —COR$^{10}$, and —CO$_2$R$^{10}$;

$R^{10}$ and $R^{11}$ are independently selected from the group consisting of: hydrogen, $C_1$-$C_6$ alkyl, monohydroxyl substituted $C_1$-$C_6$ alkyl, and phenyl;

$R^{12}$ is hydrogen or $C_1$-$C_6$ alkyl;

X is selected from the group consisting of Cl, Br, and F; and m is 1, 2, 3 or 4.

2. The compound according to claim 1, wherein G is of Formula II

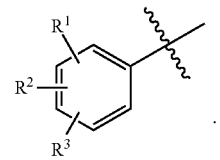

II

3. The compound according to claim 1, wherein G is of Formula II:

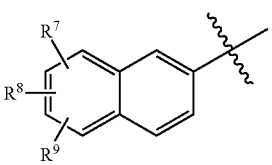

III wherein $R^1$, $R^2$, and $R^3$ are independently selected from the group consisting of: hydrogen, —NO$_2$, —Cl, and —CF$_3$; provided that $R^1$, $R^2$, and $R^3$ are not hydrogen at the same time.

4. The compound of according to claim 1, where the compound is of the formula:

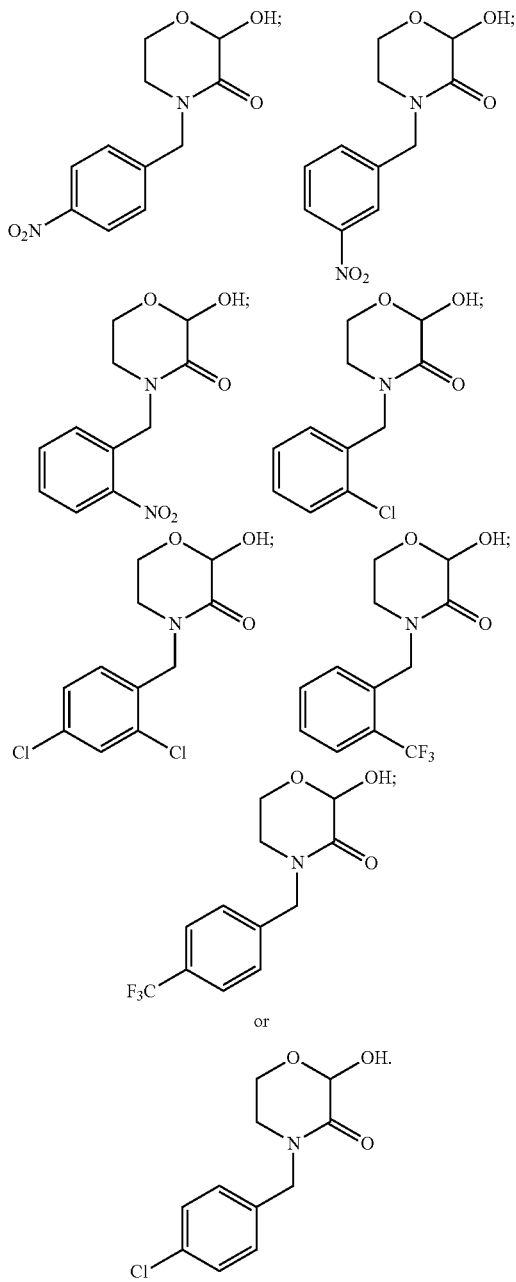

or

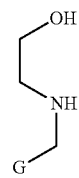

5. A method for preparing the compound according to claim 1 comprising reacting a compound of Formula IV:

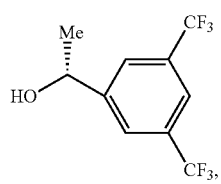

wherein G is as defined in claim 1 with an aqueous glyoxalic acid solution.

6. The method according to claim 5, wherein the step of reacting further comprises the presence of a solvent, wherein the solvent is ethyl acetate, $C_6$-$C_{12}$ alkane, benzene, toluene, paraxylene, chlorobenzene, orthodichlorobenzene, acetone, dichloromethane, chloroform, nitromethane, N,N-dimethyl formamide, dimethyl sulfoxide, 2-butanone, $C_1$-$C_6$ alcohols, 1,3-dioxane, 1,4-dioxane, tetrahydrofuran, acetonitrile, 1,2-dimethyl ethyl, water, or a mixture thereof.

7. The method according to claim 5, wherein the reaction temperature of the step of reacting is from 30 to 100° C.

8. The method according to claim 5, wherein the aqueous glyoxalic acid solution is an aqueous solution of glyoxalic acid monohydrate, or an aqueous glyoxalic acid solution with a mass ratio of glyoxalic acid to water being between 1% and 99%.

9. A method of preparing a compound of Formula IX:

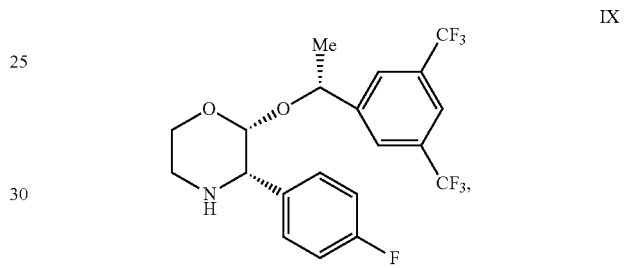

comprising:

i) reacting a compound of claim 1 with trifluoroacetic anhydride to provide a compound of Formula X:

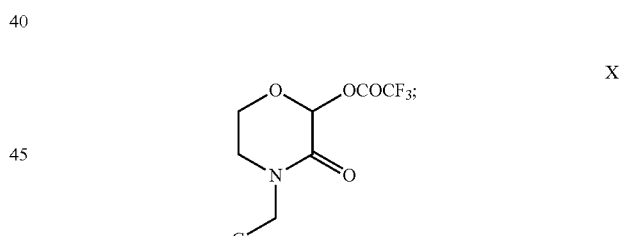

wherein G is as defined in claim 1 ii) under the catalysis of boron trifluoride, reacting the compound of Formula X with a compound of Formula XI:

XI to provide a compound of Formula XII:

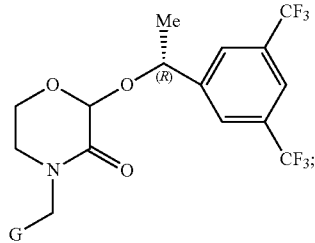

wherein G is as defined in claim 1 iii) chirally transforming the compound of Formula XII in the presence of potassium linaloolate to provide a compound of formula XIII:

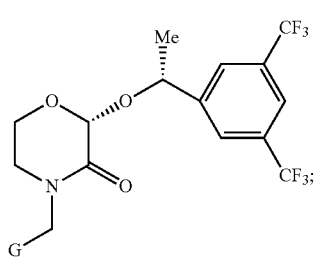

wherein G is as defined in claim 1 iv) reacting the compound of Formula XIII with p-fluorophenyl magnesium bromide; and v) hydrogenating the product of step iv) under the catalysis of palladium/carbon to provide the compound of Formula IX.

10. The compound according to claim 1, wherein $R^1$ is hydrogen, substituted or unsubstituted $C_1$-$C_6$ alkyl, substituted or unsubstituted $C_2$-$C_6$ alkenyl, $C_2$-$C_6$ alkynyl, substituted or unsubstituted phenyl, chloro, —CN, —CX$_3$, —NO$_2$, —SR$^6$, —SOR$^6$, —SO$_2$R$^6$, —(CH$_2$)$_m$—NR$^4$R$^5$, —NR$^4$COR$^5$, —NR$^4$CO$_2$R$^5$, —CONR$^4$R$^5$, —COR$^4$, —CO$_2$R$^4$, or hydroxyl.

11. The compound according to claim 1, wherein G is of Formula II:

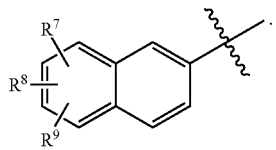

wherein:
$R^1$ is hydrogen, chloro, bromo, iodo, —CN, —CX$_3$, or —NO$_2$;
$R^2$ is hydrogen, halo, —CN, —CX$_3$, or —NO$_2$; and
$R^3$ is hydrogen, halo, —CN, —CX$_3$, or —NO$_2$;
provided that $R^1$, $R^2$, and $R^3$ are not hydrogen at the same time.

12. The compound according to claim 1, wherein G is of Formula II:

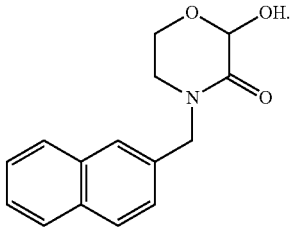 [SMILES: O=C1C(O)OCCN1Cc1ccc2ccccc2c1]

wherein each one of $R^1$, $R^2$, and $R^3$ is independently hydrogen, —NO$_2$, —Cl, or —CF$_3$, provided that 1 or 2 of $R^1$, $R^2$, and $R^3$ are not hydrogen.

13. The compound according to claim 1, wherein G is of Formula III:

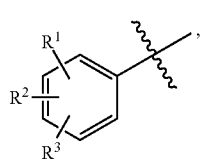

14. The compound according to claim 1, where the compound is of the formula:

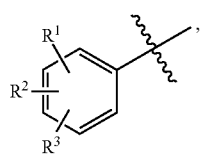

15. The method of claim 5, wherein G is of Formula II:

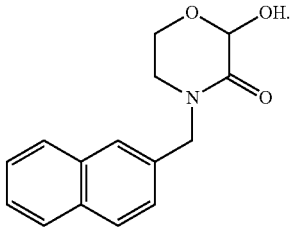

wherein:
$R^1$ is hydrogen, chloro, bromo, iodo, —CN, —CX$_3$, or —NO$_2$;
$R^2$ is hydrogen, halo, —CN, —CX$_3$, or —NO$_2$; and
$R^3$ is hydrogen, halo, —CN, —CX$_3$, or —NO$_2$;
provided that $R^1$, $R^2$, and $R^3$ are not hydrogen at the same time.

16. The method according to claim 6, wherein the solvent is N,N-dimethyl formamide, dimethyl sulfoxide, 2-butanone, $C_1$-$C_6$ alcohol, 1,3-dioxane, 1,4-dioxane, tetrahydrofuran, acetonitrile, 1,2-dimethyl ethyl, or a mixture thereof.

17. The method according to claim 6, wherein the solvent is tetrahydrofuran, acetonitrile, or a mixture thereof.

18. The method according to claim 6, wherein the solvent is tetrahydrofuran.

19. The method according to claim 7, wherein the reaction temperature is from 60 to 70° C.

20. The method according to claim 8, wherein the aqueous glyoxalic acid solution is an aqueous glyoxalic acid solution with a mass ratio of glyoxalic acid to water being 50%.

* * * * *

UNITED STATES PATENT AND TRADEMARK OFFICE
CERTIFICATE OF CORRECTION

PATENT NO.        : 9,676,736 B2
APPLICATION NO.   : 14/394041
DATED             : June 13, 2017
INVENTOR(S)       : Fuli Zhang et al.

Page 1 of 1

It is certified that error appears in the above-identified patent and that said Letters Patent is hereby corrected as shown below:

On the Title Page

Item (54) the title should be listed as follows:
4-SUBSTITUENT-2-HYDROXYLMORPHOLINE-3-ONE AND PREPARATION METHOD THEREOF In the Claims At Column 18, Line 60, the formula of Claim 3 should read:

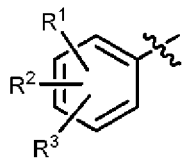

Signed and Sealed this
Seventeenth Day of October, 2017

Joseph Matal
*Performing the Functions and Duties of the*
*Under Secretary of Commerce for Intellectual Property and*
*Director of the United States Patent and Trademark Office*